United States Patent [19]

Kallet et al.

[11] 4,153,369

[45] May 8, 1979

[54] CONVERTIBLE DUAL BEAM DIFFERENTIAL SPECTROFLUOROMETER AND ABSORPTION METER

[75] Inventors: Eli A. Kallet, New York; Samuel Cravitt, Hartsdale, both of N.Y.

[73] Assignee: Farrand Optical Co., Inc., Valhalla, N.Y.

[21] Appl. No.: 850,569

[22] Filed: Nov. 11, 1977

[51] Int. Cl.$^2$ .............................. G01J 3/30; G01J 1/10
[52] U.S. Cl. ................................ 356/318; 250/461 R; 356/324; 356/246
[58] Field of Search ................ 356/73, 85, 93–95, 356/97, 104, 244, 246; 250/458, 459, 461 R, 461 B, 576

[56] References Cited

U.S. PATENT DOCUMENTS

| | | | |
|---|---|---|---|
| 3,854,050 | 12/1974 | Peterson et al. | 250/461 BX |
| 3,886,363 | 5/1975 | Ohnishi et al. | 250/461 BX |
| 3,891,853 | 6/1975 | Kremen et al. | 250/458 |
| 3,936,190 | 2/1976 | Ohnishi et al. | 250/458 |

OTHER PUBLICATIONS

Durham, III et al., *IBM Technical Disclosure Bulletin* vol. 19, No. 4, Sep. 1976, pp. 1351–1354.

*Primary Examiner*—F. L. Evans
*Attorney, Agent, or Firm*—John L. Downing

[57] ABSTRACT

A dual beam differential spectrophotometer using a rotating chopper wheel having reflective transparent, and opaque sectors transmits light alternately through standard and sample material cells for comparison. Diffuse reflectors insertable in the material cells permit the apparatus to be used either as a differential spectrofluorometer or as a differential absorption meter.

5 Claims, 5 Drawing Figures

CONVERTIBLE DUAL BEAM DIFFERENTIAL SPECTROFLUOROMETER AND ABSORPTION METER

FIELD OF THE INVENTION

The present invention relates to photometric apparatus, and more particularly to apparatus that is selectively adaptable for the measurement of fluorescence of samples or the measurement of light absorption of samples.

BACKGROUND OF THE INVENTION

Dual beam, or differential spectrophotometry involves the separation of a single beam of light into two beams, one of which is directed at a sample material or solution which may be contained in a "sample" container cell or cuvette, and the second of which is directed toward a reference material or solution which may be contained in a reference "standard" container cell or cuvetter containing only solvent or another known material. The light emitted from the two cells is then observed by one or more light detectors and compared as a function of wavelength. When the spectrofluorescence of a sample solution is to be compared with that of a reference solution the cells are arranged so that the light detector(s) receive only the fluorescent light caused by incidence of the two respective beams on the cells, and none of the excitation light directly incident upon the sample and reference cells. If, however, the light absorption properties of the sample solution are to be compared with the standard reference material, then the light incident on the two cells must be directed through the two materials so that absorption can take place, and then the unabsorbed light is directed to the light detector(s) for comparison as a function of wavelength.

Whether an apparatus is used as a differential spectrofluorometer or as a differential absorption spectrophotometer, it is important that the dual beam light paths, cells and number of reflections encountered should be as alike as possible so that no characteristic of the apparatus itself will affect the resulting comparison operation.

The present invention provides a dual beam spectrophotometer which can be converted very simply by the operator from a differential spectrofluorometer to a differential absorption spectrophotometer, and vice versa, merely by the insertion or removal of a reflective diagonal divider into or from the sample and reference container cells, or alternatively by the substitution of container cells having or not having reflective diagonals in place.

SUMMARY OF THE INVENTION

The present invention provides a light source, a light detector, first and second container cells for containing materials to be photometrically analyzed, a rotatable chopper wheel, and a mirror. The chopper wheel is positioned between the light source and mirror, and also between the first and second container cells, and contains at least one reflecting portion and one transparent portion whereby light from said source is alternately directed from said reflecting and transparent portions to said first and second container cells and light emitted from said container cells is alternately directed by said reflecting and transparent portions toward the mirror. The mirror directs the light it receives toward the light detector for comparison of the light emitted by the two container cells.

The invention further provides for selectively first and second container cells which have first and second diagonal reflectors in place, whereby light incident on the first and second container cells can, in a first mode of operation in which the reflectors are not inserted in each cell, be directed away from the mirror and light detector, and fluorescent light excited by said incident light is directed toward said light detector by the chopper wheel and mirror. In a second mode of operation in which the two reflectors are inserted into the two container cells, respectively, the light incident on the cells passes into the cells and light not absorbed by said materials is reflected by the reflectors and is directed toward the light detector by the chopper wheel and mirror.

DESCRIPTION OF THE SPECIFIC EMBODIMENT

Figure 1:
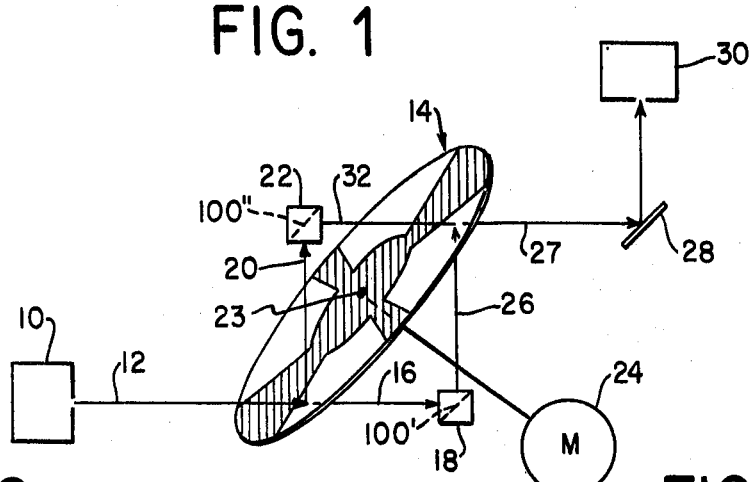
FIG. 1 is a schematic diagram of a specific embodiment of a photometric apparatus in accordance with the present invention.

The embodiment of the photometric apparatus shown in FIG. 1 includes as a light source 10 a scanning monochromator. A light beam 12 emitted from said source is directed toward a portion of a rotatable chopper wheel 14, which, as will be described in more detail hereinafter, contains transparent, reflecting and opaque portions, each of which come into line with light beam 12 as the chopper wheel 14 rotates. When the beam 12 strikes a transparent portion of the wheel 14 it passes on as light beam 16 to become incident on a first or standard reference container cell 18, which may contain a known predetermined material, such as only a solvent in which another "sample" material is to be dissolved and compared spectrofluorometrically. If, on the other hand the light beam 12 from the light source 10 strikes a reflecting portion of the chopper wheel 10, the light is redirected as light beam 20 to become incident on a second or sample container cell 22. The center 23 of the rotatable chopper wheel is connected by drive means indicated by a solid line to a motor 24 so as to rotate the wheel 14 at a desired speed.

When the transmitted light beam 16 falls on the first container cell 18 (or "cuvette") in a first mode of operation of the apparatus, it passes through the cell 18 and has no further direct effect upon the apparatus. However, in passing through the first cell 18 the light excites material in that cell to fluorescence and that fluorescent light is emitted along path 26 from the cell 18 toward a reflecting portion of the chopper wheel 14. As shown hereinafter, when light beam 12 encounters a transparent portion of chopper wheel 14 the concommittant fluorescent light 26 encounters a reflecting portion of the wheel 14, and vice versa. The fluorescent light on path 26 reflected from the chopper wheel 14 is directed along path 27 toward a mirror 28 which redirects the light to a light detector 30, such as a scanning monochromator.

Similarly, in the first mode of operation of the apparatus, light from the light source which is reflected from a reflecting portion of the chopper wheel 14 proceeds along path 20 to the second container cell and it passes through the cell and has no further direct effect upon the apparatus. However, in passing through any material in the second or sample container cell this light causes the excitation of a fluorescent emission of that material which is transmitted along path 32 to a transparent portion of the wheel 14, and through the wheel on to path 27 where it is directed by the mirror 28 toward the entrance slit of the emission monochromator or light detector 30.

Thus, in this first mode of operation, the apparatus functions as a differential spectrofluorometer with the light detector 30 alternately receiving fluoresced light from the first or reference container cell 18 and fluorescent light from the sample container cell 20. The light received by the light detector 30 can then be compared in intensity as a function of wavelengths by means of plotter oscilloscope or other means not shown.

In practice, the light source 10 and the mirror 28 are positioned relative to the chopper wheel so that the input light beam on path 12 is separated by 90° around the circumference of the chopper wheel from the light path 27 which is directed by the mirror 28 to the light detector 30.

Figure 2:
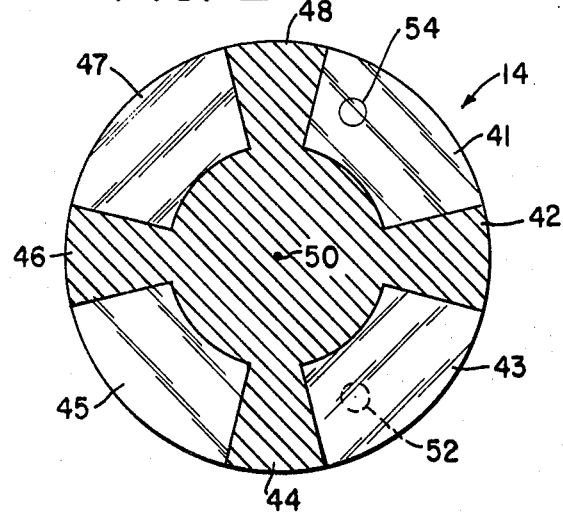
FIG. 2 is a plan view of a chopper wheel used in the embodiment of FIG. 1.

The chopper wheel 14 is shown in more detail in FIG. 2. The wheel 14 has eight sectors around its circumference: a 62° transparent sector 41, a 28° opaque sector 42, a 62° reflecting sector 43, a 28° opaque sector 44, a 62° transparent sector 45, a 28° opaque sector 46, a 62° reflecting sector 47 and a 28° opaque sector 48. The sectors 41-48 have a radial width of one-half of the radius of the chopper wheel 14 and the central portion of the wheel 14 is entirely opaque. Although the transparent sectors 41 and 45 pass light directly through the chopper wheel 14, the reflecting sectors 43 and 47 reflect incident light equally from either side of the wheel 14. In practice, the chopper wheel 14 is formed as a sandwich of the two quartz glass discs separated by aluminized and opaque sections. The outer and inner rims of the wheel are sealed to prevent moisture or foreign substances from entering the interior and altering its optical characteristics. The hub 50 of the wheel 14 is connected by a shaft (not shown) to motor 24.

As described hereinbefore, the light incident upon the chopper wheel 14 is displaced 90° around the circumference of the wheel 14 from the light which proceeds from the wheel through the process of reflection or transmission to the mirror 28 and thence to the light detector 30. Thus, the dotted circle 52 indicates in cross section the light beam incident along path 12 which is either transmitted through the wheel 14 to the sample container cell 18 or is reflected by the wheel 14 toward the reference standard container cell 22. Similarly, the dotted circle 54 shows the cross section of the light beam on path 27 which is directed to the mirror 28 and the light detector 30. The angular width of the opaque portions (42, 44, 46, 48) is chosen to be greater than the width of the light beams reflected from and transmitted through the chopper wheel 14, so that no light from the light source 10 or fluorescent light would ever be partially transmitted and partially reflected at the same time by the apparatus.

FIG. 1 also shows first and second reflectors 100' and 100" which can be placed diagonally in the first and second container cells 18 and 22, respectively to convert the apparatus to a second mode of operation, namely one in which it functions as a spectro-absorption meter.

Figure 3:
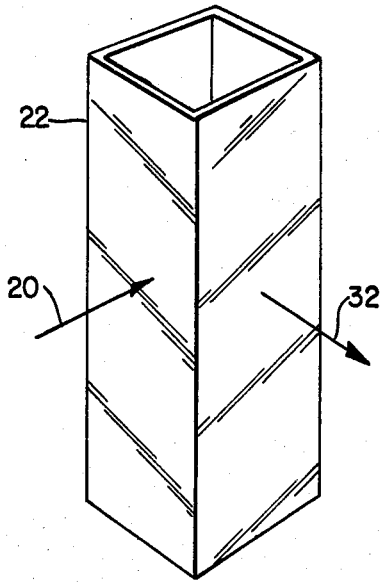
FIG. 3 is a perspective view of a container cell used in the embodiment of FIG. 1.

FIG. 3 shows the sample container cell 22 in the first mode of operation.

Figure 4:
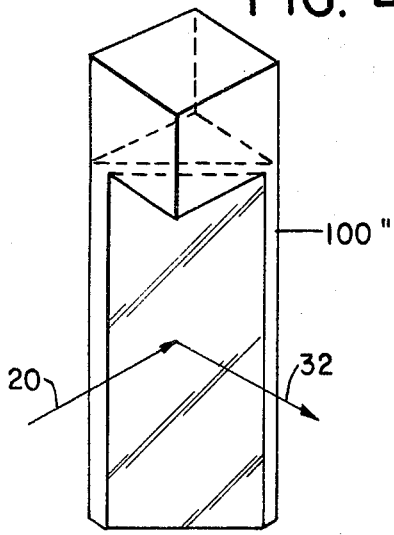
FIG. 4 is a perspective view of a diagonal reflector for insertion in the container cell of FIG. 3.
Figure 5:
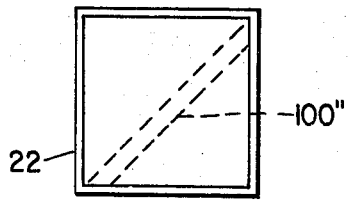
FIG. 5 is a top view of the container cell and insertable reflector of FIG. 4.

FIGS. 4 and 5 show the sample container cell 22 and mirror 100" in place functioning in this second mode of operation. It will become obvious from the discussion that the first or reference container cell 16 with mirror 100' in place functions in a completely analogous manner.

FIG. 3 shows the sample container cell 22 functioning in the first mode of operation with no diagonal mirror 100" in place. The sample cell 22 is a hollow, thin walled rectangular container with an open top and closed base. The cell 22 is 45 mm. in length with a 10 mm. by 10 mm. cross section; and is made of a transparent material such as quartz, glass, or clear plastic. In FIG. 3 the light beam 20 reflected from the chopper wheel 14 passes directly through the cell 22. In its transit, the beam 20 excites any material in cell 20 to fluoresce, and a portion of the fluorescent light so excited is emitted along path 32 toward a transparent section of the chopper wheel 14.

FIGS. 4 and 5 show perspective view and top views, respectively, of the diagonal reflector 100" and sample container 22 in the second mode of operation. The incident light beam 20 reflected from a reflective portion of the chopper wheel 14 passes into the cell 22 and at least a portion thereof is reflected by the reflector 100" along path 32 toward a transparent portion of the wheel 14, mirror 28 and light detector 30. The light entering the sample cell 22 is partially absorbed by any material within the cell and the intensity of the light transmitted along path 32 is a function of the absorption properties of that material, the incident intensity, and the cell path length.

As noted above, FIGS. 3, 4, and 5 are also completely representative of the operation of the reference cell container 18, in the two modes of operation, the diagonal reflector 100' being positioned in the second mode of operation to reflect the light transmitted through the chopper wheel 14 directly onto path 26 and thence to a reflecting portion of the wheel 14, path 17, mirror 28 and light detector 30.

It will be obvious to those skilled in the art that the first and second reflectors 100' and 100" can be selectively insertable and removable into and from the first and second container cells 18, 22 respectively, to convert the function of the apparatus of this invention between first and second modes of operation, or alternatively, the first and second container cells 18 and 22 can be exchanged for container cells with diagonal reflectors 100' and 100" fixed in place.

Finally, it has been found that when the apparatus of this invention is to be used in the second mode of operation, i.e., as a differential spectro-absorption meter, the two reflectors 100' and 100" should advantageously be diffuse reflectors rather than specular reflectors, and therefore, their reflecting surfaces are preferably finely ground.

What is claimed is:
1. Differential photometric apparatus comprising:
a light source positioned on one side of a rotatable mask to illuminate a portion of said mask, said rotatable mask having at least one transparent portion and at least one reflecting portion; a first container cell positioned on said one side of said mask to receive light from said light source reflected from a reflecting portion of said mask, and to emit light perpendicularly from said incident light toward a transparent portion of said mask; a second container cell positioned on another side of said mask to receive light from said light source through a transparent portion of said mask and to emit light perpendicularly from said light so incident toward a reflecting portion of said mask on said other side of said mask; a mirror positioned on said other side of said mask to receive light transmitted from said first container cell through a transparent portion of said mask, and light transmitted from said second container cell to a reflecting portion on the other side of said mask and said mirror redirecting said transmitted and reflected light toward a light detector; and means for rotating said mask; and further comprising a selectively insertable first reflector adapted to be inserted in said first container cell for reflecting light incident from said light source on said first cell toward said one side of said mask; and a second selectively insertable second reflector adapted to be inserted in said second container cell for reflecting light from said light source incident on said second cell toward the other side of the mask.

2. Differential photometric apparatus according to claim 1 wherein said light source comprises a scanning monochromator and said light detector comprises a scanning monochromator.

3. Differential photometric apparatus according to claim 1 wherein said rotatable mask has an opaque portion separating each transparent and reflecting portion, each said opaque portion being at least as large as any beam of light from said light source incident on said mask, and as any beam of light transmitted through said mask, and as any beam of light reflected from the other side of said mask toward said mirror.

4. Differential photometric apparatus selectively convertible from a differential spectrofluorometer to a differential absorption meter comprising:
first and second rectangular cells for holding solutions to be photometrically analyzed;
first and second selectively insertable reflectors for respective insertion along the diagonals of said first and second cells.

5. Differential photometric apparatus comprising a light source positioned on one side of a rotatable chopper wheel having at least one transparent portion and at least one reflecting portion, a light detector positioned on the other side of said wheel, first and second container cells for containing solutions to be photometrically analyzed each positioned on opposite sides of said wheel; wherein light from said light source is alternately directed toward said first and second container cells by said chopper wheel and light emitted from said container cells is alternately directed toward said light detector by said chopper wheel and a mirror, said apparatus further comprising first and second reflectors which are selectively positioned diagonally in said first and second container cells, respectively, whereby light incident on said first and second container cells can in a first mode of operation be directed away from said chopper wheel, mirror and light detector, and fluorescent light excited by said incident light is directed toward said chopper wheel, mirror and light detector; and in a second mode of operation light incident on said first and second container cells passes into said cells and is directed by said first and second reflectors positioned in said cells, respectively, toward said chopper wheel, mirror and light detector.

* * * * *